United States Patent
Echarri

(10) Patent No.: US 8,986,224 B2
(45) Date of Patent: Mar. 24, 2015

(54) GUIDEWIRE WITH HIGHLY FLEXIBLE TIP

(75) Inventor: Roberto Echarri, Miami, FL (US)

(73) Assignee: Depuy Synthes Products, LLC, Raynham, MA (US)

( * ) Notice: Subject to any disclaimer, the term of this patent is extended or adjusted under 35 U.S.C. 154(b) by 216 days.

(21) Appl. No.: 13/554,981

(22) Filed: Jul. 20, 2012

(65) Prior Publication Data

US 2014/0024968 A1   Jan. 23, 2014

(51) Int. Cl.
*A61B 5/00*   (2006.01)
*A61M 25/00*   (2006.01)
*A61M 25/09*   (2006.01)

(52) U.S. Cl.
CPC ......... *A61M 25/09* (2013.01); *A61M 25/09033* (2013.01)
USPC ....................................................... 600/585

(58) Field of Classification Search
USPC .............. 600/585, 434, 16; 606/159; 604/529
See application file for complete search history.

(56) References Cited

U.S. PATENT DOCUMENTS

| | | | |
|---|---|---|---|
| 4,691,746 A | 9/1987 | Sedgewick | |
| 5,253,653 A * | 10/1993 | Daigle et al. | 600/585 |
| 5,376,083 A | 12/1994 | Mische | |
| 5,892,166 A | 4/1999 | Sanderson | |
| 6,206,753 B1 | 3/2001 | Werner | |
| 6,338,736 B1 | 1/2002 | Boosfeld et al. | |
| 7,055,812 B2 | 6/2006 | Balsells | |
| 7,340,878 B2 | 3/2008 | Rozenvasser et al. | |
| 7,412,993 B2 | 8/2008 | Tzeng | |
| 2002/0032391 A1 * | 3/2002 | McFann et al. | 600/585 |
| 2004/0082881 A1 | 4/2004 | Grewe et al. | |
| 2005/0165366 A1 | 7/2005 | Brustad et al. | |
| 2005/0250976 A1 * | 11/2005 | Melvin et al. | 600/16 |
| 2007/0060846 A1 | 3/2007 | Hardin | |
| 2009/0069836 A1 | 3/2009 | Labdag et al. | |
| 2009/0156999 A1 | 6/2009 | Adams et al. | |

FOREIGN PATENT DOCUMENTS

EP   778038 A2   6/1997
EP   1243283 A2   9/2002

OTHER PUBLICATIONS

EPO, European Search Report in European Patent Application No. 13177317.8 dated Oct. 31, 2013.

* cited by examiner

*Primary Examiner* — Brian Szmal

(57) ABSTRACT

A medical device formed of a coil with repeating loops, each loop forming a polygon and each successive loop being slightly rotated with respect to its adjacent loops to form a spiral configuration. The polygon in a preferred embodiment is a triangle, and the repeating triangular loop coil can be used as a guidewire in a stent delivering catheter. The guidewire can further include a stiff core wire that is disposed within the triangular loop coil, where the stiff core wire includes tapered sections that reduce the stiffness in the distal direction. The coil can include multiple sections of different loop shapes, including circular, to alter the stiffness of the guidewire to meet the needs of the application.

6 Claims, 4 Drawing Sheets

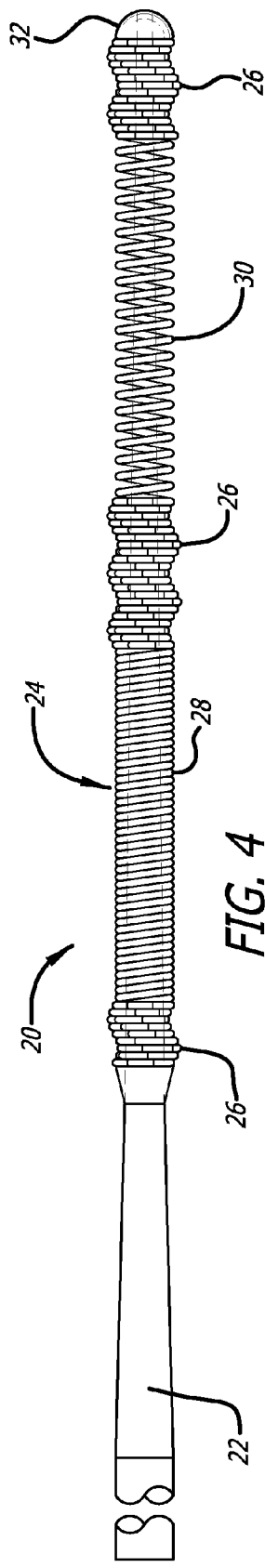
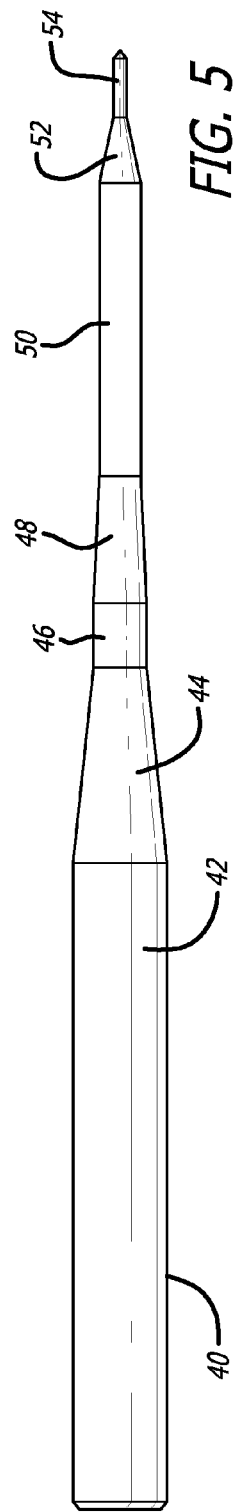
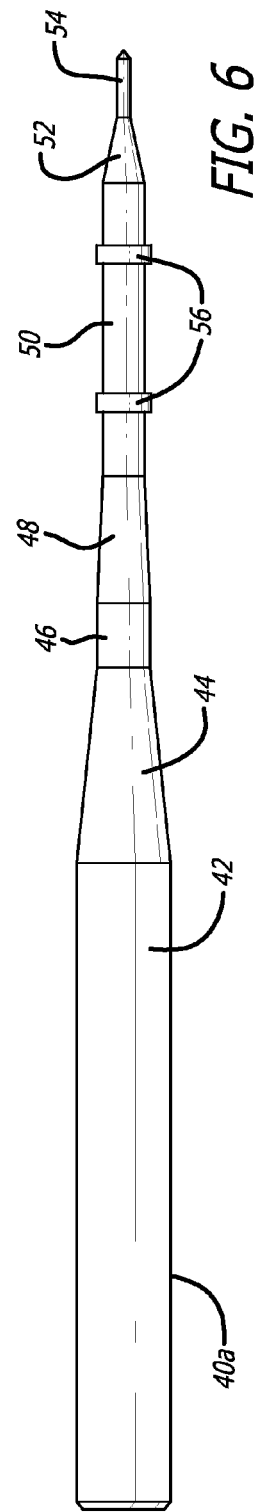

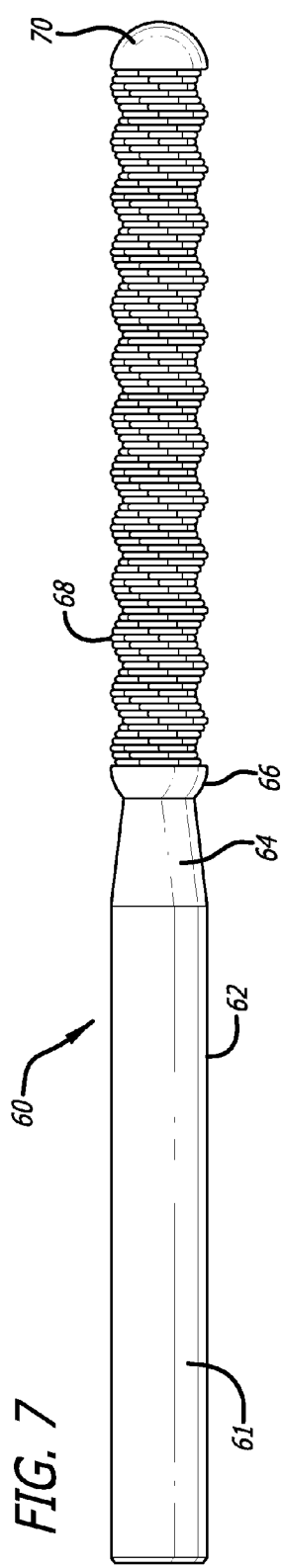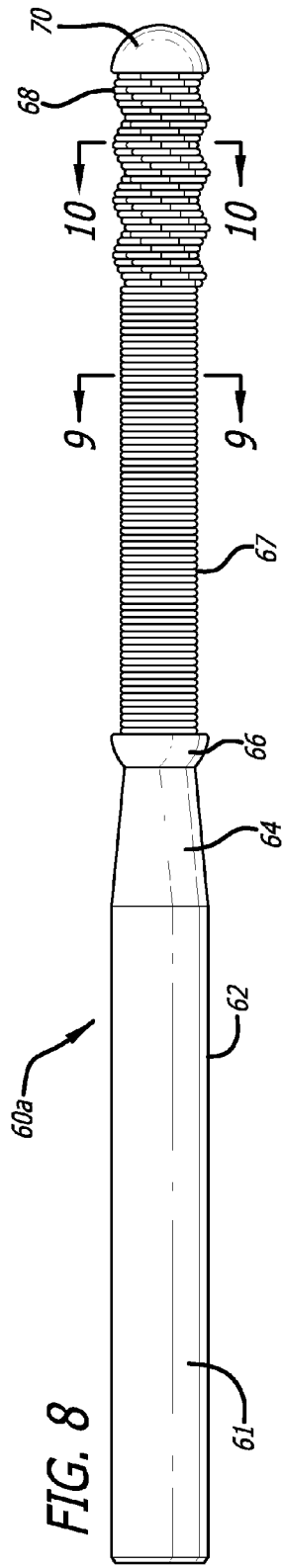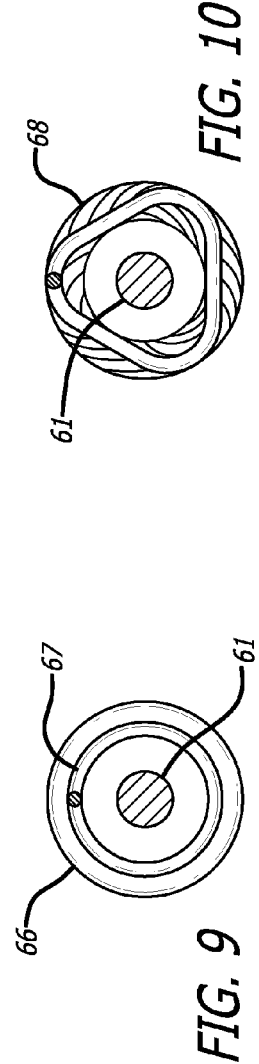

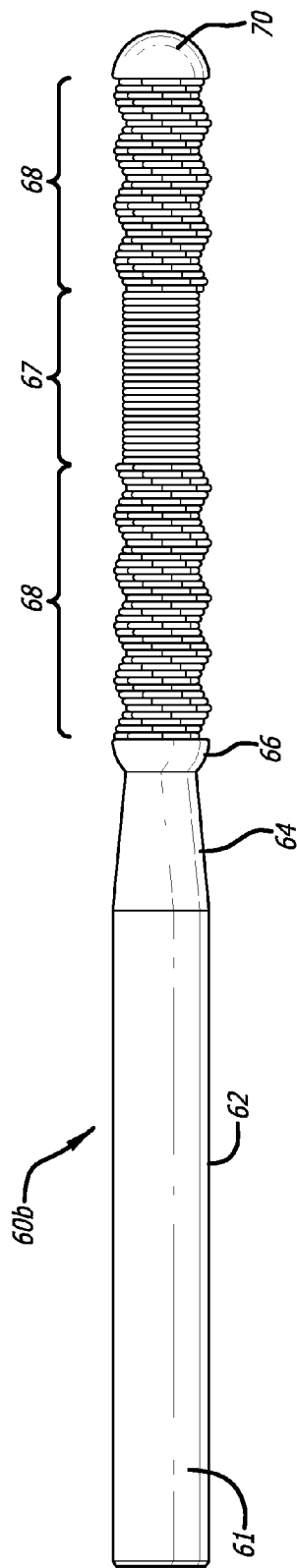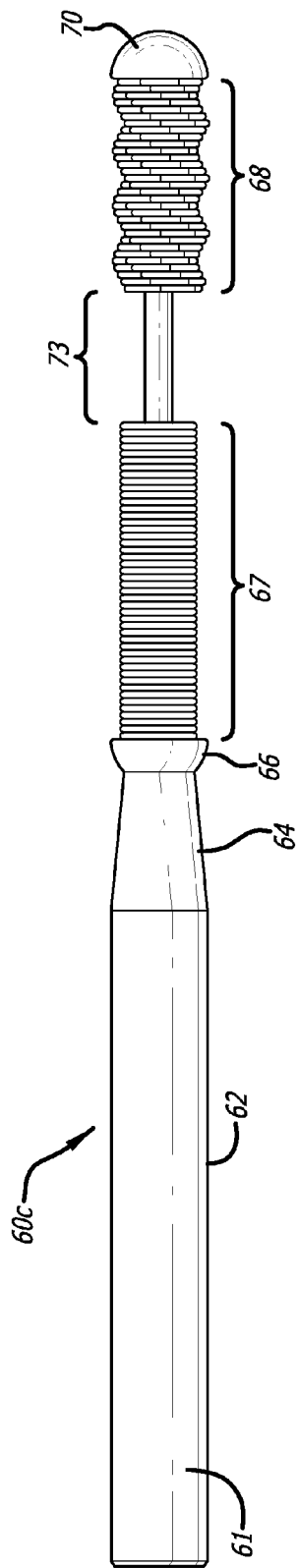

GUIDEWIRE WITH HIGHLY FLEXIBLE TIP

BACKGROUND

1. Field of the Invention

This invention relates generally to vascular interventional medical devices, and more particularly concerns guide wires for use in a therapeutic system or for delivery of medical devices.

2. Description of Related Art

Conventional minimally invasive catheter based therapies, including those used for stent delivery, typically require guidewires that are one to two meters long extending through a longitudinal lumen in the catheter, and that are torqueable and pushable at the proximal end, yet soft and flexible at the distal end. Many such guidewires are made of stainless steel or the like, and are ground to tapers which provide the desired bending properties along the guidewire. It is useful for such guidewires to be torqueable from the base of the guidewire for manipulation of the distal tip, which is typically bent, for guiding the distal tip through vascular passages. While such guidewires need to be torqueable, pushable and resilient, particularly at the proximal regions of the guidewire, they also need to be flexible, particularly at the distal regions of the guidewire.

SUMMARY OF THE INVENTION

The present invention related to a guidewire that has improved flexibility, particularly at the tip where navigation of the guidewire is critical, and methods for manufacture of such guidewires. In particular, the guidewire of the present invention is a coil that forms a polygonal loop in the transverse (or cross-sectional) direction as it extends in the longitudinal direction, and preferably a triangular loop in transverse direction that may be disposed about a core member. The polygonal section may alternate with a circular section, and the two types of sections may be intermittent, continuous, or some other combination. The core section may have a plurality of contiguous tapered segments so as to produce a linear change in the stiffness of the guidewire over a longitudinal portion of the device. Alternatively, the core member may have a continuously diminishing taper to produce a curvilinear profile and a linear change in the stiffness over the entire taper section.

The above summary of some of the embodiments is not intended to describe each disclosed embodiment or every implementation of the present invention. The included figures, and detailed description set forth below, more particularly exemplify the embodiments of the inventions.

BRIEF DESCRIPTION OF THE DRAWINGS

FIG. 4 is a side view, partially in phantom, of a multi-configuration guidewire and core member;

FIG. 5 is a side view of a core member with multiple tapered sections;

FIG. 6 is a side view of an alternate core member with first and second collars;

FIG. 7 is a side view of a core and guidewire combination with a triangular loop throughout;

FIG. 8 is a side view of a core and guidewire combination with circular and triangular loops;

FIG. 9 is a cross sectional view taken along line 9-9 of FIG. 8;

FIG. 10 is a cross sectional view taken along line 10-10 of FIG. 8;

FIG. 11 is a side view of a core and guidewire combination with alternating triangular and circular loops; and FIG. 12 is a side view of a core and guidewire combination with intermittent circular and triangular loops.

DETAILED DESCRIPTION OF THE PREFERRED EMBODIMENTS

Figure 1:
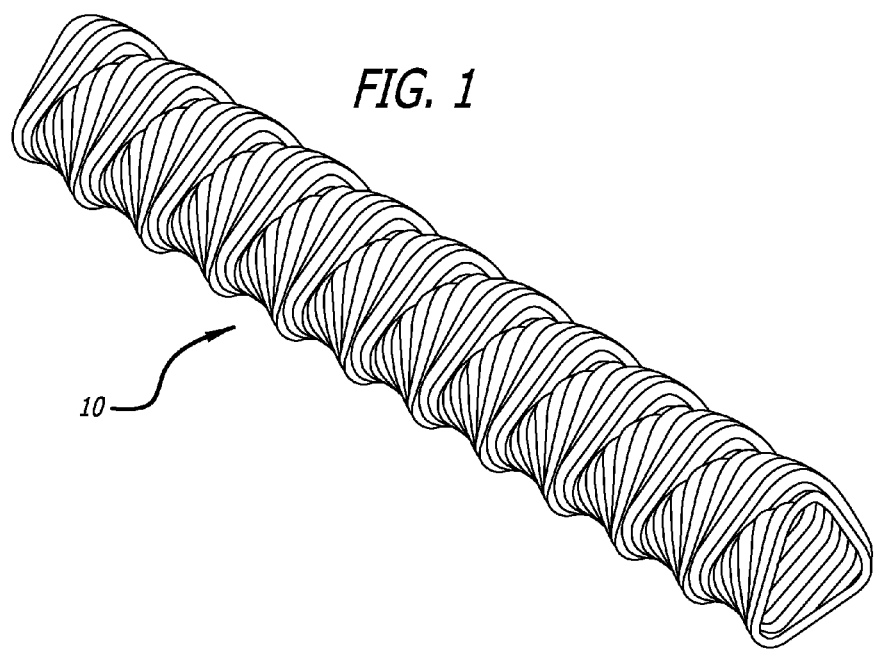
FIG. 1 is an elevated, perspective view of a first embodiment of the guidewire of the present invention.
Figure 2:
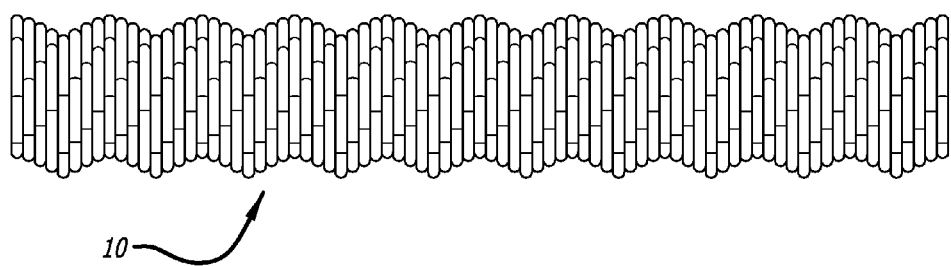
FIG. 2 is a side view of the embodiment of FIG. 1.
Figure 3:
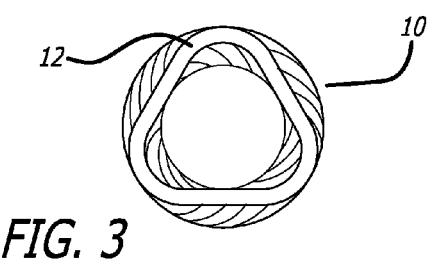
FIG. 3 is an axial view of the embodiment of FIG. 1.

Guidewires used for vascular therapeutic intervention typically need to be torqueable, pushable and resilient over a proximal region of the guidewire, and flexible, over the distal region of the guidewire. While tapered guidewires can provide a range of proximal stiffness and torqueability to distal flexibility, enhancement of the proximal stiffness of such guidewires can give a physician manipulating the guidewire better control over the distal positioning of the guidewire. The present invention solves these issues in a unique and novel manner. FIGS. 1-3 illustrate a guidewire coil 10 that is formed with continuous loops having a polygonal, and more particularly a triangular, shape. Each triangular loop 12 is slightly rotationally displaced with respect to the immediately adjacent triangular loop to produce a spiral pattern as shown in FIG. 1. The amount of rotational displacement can vary with the application, producing a tighter or looser spiral configuration.

The triangular shape of the loop in the coil produces an enhanced flexural modulus, elastic modulus, and tensile strength over a simple circular coil. The triangular loop provides the benefit of, when placed inside a circular catheter lumen, preventing buckling of the wire without restricting flow to the extent of a circular cross-sectional guidewire. Other polygonal loops are possible, including square, pentagonal, and hexagonal. However, the triangular loop has been found to provide the most advantage in strength and flexure properties.

Different sequences and combination of coils can be configured to produce a linear change in stiffness over a longitudinal portion of the guidewire. For example, a softer guidewire can be safely and successfully delivered further into tortuous or delicate vascular paths such as in the brain or cardiac vasculature allowing treatment to patients that could not be treated before. The present feature allows the guidewire to be safely delivered during a neurological or cardiac procedure where it is used as a path for other medical devices.

FIG. 4 illustrates a guidewire 20 comprising a core wire 22 that is typically coated with a lubricious coating such as PTFE or other similar coating. The core wire 22 includes a taper, or diminishing radial component, in the proximal to distal direction to yield a more flexible core at the distal end of the guidewire 20. The tapering section can be continuous, segmented, or combinations thereof as the application and conditions of the vasculature require. Over the core wire 22 is a coil 24 that may include multiple sections having different transverse shapes. In the guidewire of FIG. 4, the coil 24 includes in the proximal to distal direction a triangular coil section 26, a circular coil section 28, another triangular coil section 26, a circular coil 30 with a looser wind, another triangular coil 26, and an end cap 32. Using different lengths and different wind characteristics, a more precise flexure and strength profile can be created to suit the needs of the patient or application. However, it is desirable to ensure that the transition length between the flexible tip to the stiffer core wire be sufficiently subtle because too abrupt of a transition can cause tracking difficulties.

FIGS. 5 and 6 illustrate a core wire 40 with various taper sections to control the flexure of the guide wire. The proximal end 42 of the core 40 is cylindrical, or constant radius, and is connected at its distal end to a first, moderately tapered section 44. The tapered section 44 is joined to a second cylindrical section 46, followed by a second tapered section 48. A third and final cylindrical section 50 and taper section 52 complete the core wire 40, terminating in a pin 54 for connecting the end cap 32. In FIG. 6, the core 40a includes ribs 56 or extensions that facilitate the centering of the filler coils as well as axial positioning during manufacture. These ribs 56 also act as positioning marks as well as additional push/pull support for stents and other devices being delivered through the patient's vasculature. The core can take many other forms and having continuous, segmented, and alternating taper sections that vary in both number and degree.

FIG. 7 illustrates another example of a guidewire 60 of the present invention, comprising a core 61 having a proximal cylindrical section 62, an tapered fitting 64 including a parabolic proximal cap 66, and an end cap 70. In between the proximal cap 66 and the end cap 70 is a triangular coil 68 that captures the distal end of the core wire 61 inside each triangular loop. The guidewire 60a of FIG. 8 is similar to the guidewire 60 of FIG. 7, but includes a circular loop section 67 in addition to the triangular loop section 68. As shown in FIGS. 9 and 10, the core wire 61 is captured within the circular loop 67 and the triangular loop 68 along the length of the guidewire 60a. In FIG. 11, the guidewire 60b has two triangular loop portions 68 sandwiching a circular loop section 67. In FIG. 12, the guidewire 60c has a circular loop section 67 and a triangular loop section separated by a gap 73 in the coil.

The ability to pass through narrowed, or stenosed, lesion areas is vital to the guidewire function. Inability to pass through to the target area derails any successful procedure. This challenge is addressed by the present invention, which combines a stiffer core body with a more flexible tip. A softer tip guidewire can be successfully and safely delivered further into the brain or heart vasculature and can allow treatment of some patients that otherwise would have no options. The present invention reduces the risk of puncture the blood vessel with the guidewire tip during a surgical procedure due to the soft nature of the tip. The triangular coil also reduces the delivery force by reducing the points of contact with the access device inner diameter while increasing the flow of any liquid through the catheter while the guidewire is in place. That is, the delta or triangular profile creates gaps that can allow fluid to flow through the catheter while the guidewire is in place.

I claim:

1. A medical device comprising a coil formed of successive polygons, each polygon rotationally displaced from its adjacent polygons to form a spiral configuration, wherein the polygon is a triangle, the medical device is a guidewire, within the coil is a core wire extending therein through, the core wire has at least one taper section between a proximal and distal end the polygon is a triangle, the coil further includes a circular loop section in addition to the triangular loops.

2. The medical device of claim 1, wherein the core wire is stiffer at a proximal end than at a distal end.

3. The medical device of claim 1, wherein the core wire includes first and second spaced apart ribs.

4. The medical device of claim 1, wherein the coil further includes a circular loop section in addition to the triangular loops.

5. The medical device of claim 1, wherein the circular loop section is sandwiched in between two triangular loop sections.

6. The medical device of claim 1, wherein the circular loop section is spaced from the triangular loops by a gap in the coil.

* * * * *